US010058594B2

(12) United States Patent
Hicks, Jr. et al.

(10) Patent No.: US 10,058,594 B2
(45) Date of Patent: *Aug. 28, 2018

(54) TREATMENT OF DEPRESSION AND PTSD

(71) Applicant: Neuralight HD, LLC, Phoenix, AZ (US)

(72) Inventors: Edson Conrad Hicks, Jr., Phoenix, AZ (US); Constance T. Dutton, San Diego, CA (US)

(73) Assignee: Neuralight HD, LLC, Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/268,979

(22) Filed: Sep. 19, 2016

(65) Prior Publication Data
US 2017/0224782 A1 Aug. 10, 2017

Related U.S. Application Data

(63) Continuation of application No. 14/436,172, filed as application No. PCT/US2013/065711 on Oct. 18, 2013, now abandoned.

(60) Provisional application No. 61/715,590, filed on Oct. 18, 2012.

(51) Int. Cl.
| A61K 38/00 | (2006.01) |
| A61K 47/00 | (2006.01) |
| A61K 38/24 | (2006.01) |
| A61K 9/00 | (2006.01) |

(52) U.S. Cl.
CPC ............ *A61K 38/24* (2013.01); *A61K 9/0019* (2013.01)

(58) Field of Classification Search
CPC .............................. A61K 38/24; A61K 9/0019
See application file for complete search history.

(56) References Cited

U.S. PATENT DOCUMENTS

| 4,665,161 A | 5/1987 | Yoki et al. |
| 4,689,222 A | 8/1987 | McMichael |
| 4,968,299 A | 11/1990 | Ahlstrand et al. |
| 5,384,132 A | 1/1995 | De Meets et al. |
| 5,677,275 A | 10/1997 | Lunardi-Lskandar et al. |
| 5,700,781 A * | 12/1997 | Harris .................... A61K 38/24 424/188.1 |
| 5,929,028 A | 7/1999 | Skrahanja et al. |
| 6,706,681 B1 | 3/2004 | Samaritani |
| 7,101,847 B2 | 9/2006 | McMichael |
| 7,122,198 B1 | 10/2006 | Singh et al. |
| 7,405,197 B2 | 7/2008 | Menezo |
| 7,605,122 B2 | 10/2009 | Tuntland |
| 8,143,220 B2 | 3/2012 | Weiss et al. |
| 8,652,189 B2 | 2/2014 | Gaftii et al. |
| 8,680,086 B2 | 3/2014 | Hicks, Jr. et al. |
| 8,680,088 B2 | 3/2014 | Hicks, Jr. et al. |
| 2002/0058656 A1 | 5/2002 | Ockert |
| 2002/0123670 A1 | 9/2002 | Goetzke et al. |
| 2004/0072731 A1 | 4/2004 | McMichael |
| 2006/0258568 A1 | 11/2006 | Huber |
| 2007/0026027 A1* | 2/2007 | Tuntland ............. A61K 9/0056 424/400 |
| 2008/0039389 A1 | 2/2008 | Weiss et al. |
| 2008/0318871 A1 | 12/2008 | Khan et al. |
| 2009/0081205 A1 | 3/2009 | Weiss et al. |
| 2010/0004172 A1 | 1/2010 | Khan et al. |
| 2011/0082384 A1 | 4/2011 | Harte et al. |
| 2011/0224140 A1* | 9/2011 | Belluscio .............. A61K 38/24 514/9.7 |
| 2012/0071408 A1 | 3/2012 | Santasiero |
| 2012/0265129 A1 | 10/2012 | Hicks, Jr. et al. |
| 2012/0265712 A1 | 10/2012 | Hicks, Jr. et al. |
| 2013/0196914 A1 | 8/2013 | Hicks, Jr. et al. |
| 2015/0057224 A1 | 2/2015 | Hicks, Jr. et al. |
| 2015/0290293 A1 | 10/2015 | Hicks, Jr. et al. |
| 2016/0339083 A1 | 11/2016 | Hicks, Jr. et al. |

FOREIGN PATENT DOCUMENTS

| EP | 0144489 | 6/1985 |
| JP | 2005-501918 | 1/2005 |
| JP | 2006-504735 | 2/2006 |
| WO | WO 2003022302 | 3/2003 |
| WO | WO 2004032954 | 4/2004 |
| WO | WO 2004069271 | 8/2004 |

OTHER PUBLICATIONS

US 7,488,594, 02/2009, Saxena et al. (withdrawn)
Ghosh et al. Products, Technologies, and Development Issues, Oct. 2, 2005 vol. 29, Issue 10.
Janicki "Chronic Pelvic Pain as a Form of Complex Regional Pain Syndrome. Role of Autonomic Nervous System in Chronic Pelvic Pain," vol. 77, Supplement I. Feb. 2002, p. S51.
Abdallah et al., "Human fetal nongonadal tissues contain human chorionic gonadotropin/luteinizing hormone receptors." *J Clin Endocrinol Metab.*, 89(2):952-956, Feb. 2004.
Al-Hader et al., "Novel expression of functional luteinizing hormone/chorionic gonadotropin receptors in cultured glial cells from neonatal rat brains," *Biol Reprod.*, 56(2):501-507, Feb. 1997.
Anonymous, "HCG hormone therapy may benefit patients with intractable pain," News-Medical.net, Mar. 25, 2011, pp. 1-2 Retrieved from the Internet: <URL: http://www.news-meclical.net/news/20110325/hcg-hormone-therapy-may-benefit-patients-with-intractable-pain.aspx>.
Anonymous, "Injection Method," hcginfoonline, 2007, Retrieved from the Internet on Feb. 23, 2017: <URL: http://www.hcginfoonline.com/Injection%20method.htm>.
Apkarian et al., "Pain arid the brain: specificity and plasticity of the brain in clinical chronic pain," *Pain.* 152(3 Suppl):S49-64 Epub Dec. 2010.

(Continued)

*Primary Examiner* — Marcela M Cordero Garcia
(74) *Attorney, Agent, or Firm* — Fish & Richardson P.C.

(57) ABSTRACT

Depression and PTSD are treated by administration of hCG, or an hCG analog, or a prodrug or metabolite of hCG or an hCG analog, in an amount equivalent to a subcutaneous dose of 50-200 IU, preferably 120-170 IU, more preferably 140-160 IU, of hCG per day.

13 Claims, No Drawings

(56) References Cited

OTHER PUBLICATIONS

Bair et al., "Association of depression and anxiety alone and in combination with chronic musculoskeletal pain in primary care patients," *Psychosom Med.*, 70(8).890-897. Epub Sep. 2008.
Berge et al., "Pharmaceutical salts," *J Pharm Sci.*, 66(1):1-19, Jan. 1977.
Bradley, "Pathophysiology of fibromyalgia," *Am J Med.*, 122(12 Suppl):522-30, Dec. 2009.
Colucci-D'Amato et al., "The end of the central dogma of neurobiology: stem cells and neurogenesis in adult CNS," *Neurol Sci.*, 27(4):266-270, Sep. 2006.
Costigan et al., "Neuropathic pain: a maladaptive response of the nervous system to damage," *Annu Rev Neurosci.*, 32:1-32, 2009.
David. "Injection Method" 2007 [retrieved on Mar. 19, 2013] Retrieved from the Internet: <URL: http://www.hcginfoonline.com/Injection%20method.htm> , 5 pages.
Decker et al., "Different thresholds of tissue-specific dose-responses to growth hormone in short prepubertal children," *BMC Endocr Disord.*, 12:26, 9 pages, Nov. 1, 2012.
European Office Action in International Application No. EP12771099.4, dated Mar. 23, 2017, 7 pages.
European Search Report for EP App. No. 12 77 1099, dated Oct. 6, 2914, 9 pages.
Foulkes and Wood, "Pain Genes," *PLoS Genet.*, 4(7): e1009086. doi:10.1371/journal.pgen.1000086, Jul. 2008.
Fox, "Patients with intractable pain report relief using HCG," *Medscape*, Mar, 28, 2011, Retrieved from the Internet: URL: http://www.medscape.com/viewarticle/739739>, 3 pages.
Fox, "Patients With Intractable Pain Report Relief Using HCG," Mar. 28, 2011, Retrieved from the Internet: <URL: http://www.medscape.com/viewarticle/739739>, 3 pages.
Gallego et al., "The pregnancy hormones human chorionic gonadotropin and progesterone induce human embryonic stem cell proliferation and differentiation into neuroectodermal rosettes," *Stem Cell Res Ther.*, 1(4):28, Sep. 2010.
Greene and Tischler, "Establishment of a noradrenergic clonal line of rat adrenal pheochromocytoma cells which respond to nerve growth factor," *Proc Natl Acad Sci U S A.*, 73(7):2424-2428, Jul. 1976.
Hashimoto et al., "Chorionic Gonadotropin Preparation as an Analgesic", Archives of Internal Medicine, Feb. 1981, vol. 141, downloaded from www.archinternmed.com.
Hicks et al., "Daily Low Dose HCG: Neuroplasticity and Chronic Rain Control", Pain Article, Jun. 21, 2011.
Hu et al., "Essential Role of G Protein-gated Inwardly Rectifying Potassium Channels in Gonadotropin-induced Regulation of GnRH Neuronal Firing and Pulsatile Neurosecretion", The Journal of Biological Chemistry, Sep. 1, 2006 vol. 281, No. 35, pp. 25231-25240.
Huber et al., "Effect of highly purified human chorionic gonadotropin preparations on the gene expression signature of stromal cells derived from endometriotic lesions: potential mechanisms for the therapeutic effect of human chorionic gonadotropin in vivo", Fertility and Sterility, Oct. 2, 2007, vol. 88, No. 2, pp. 1232-1239.
International Preliminary Report on Patentability for PCT/US2012/033828, dated Oct 15, 2013, 6 pages.
International Preliminary Report on Patentability for PCT/US2013/065711 dated Apr. 30, 2015, 12 pages.
International Search Report and Written Opinion for PCT/US2013/065711 dated Feb. 13, 2014, 10 pages.
International Search Report and Written Opinion for PCT/US2015/060348 dated May 12, 2016, 7 pages.
International Search Report in PCT/US2012/33828 dated Sep. 21, 2012, 4 pages.
Kashyap et al., "Assisted reproductive technology and the incidence of ovarian cancer: a meta-analysis," *Obstet Gynecol.*, 103(4):785-794, Apr. 2004.
Kawasaki et al., "Cytokine Mechanisms of Central Sensitization:. Distinct and Overlapping Role of Interleukin-1 B, Interleukin-6, and Tumor Necrosis Factor-a in Regulating Synaptic and Neuronal Activity in the Superficial Spinal Cord", The Journal of Neuroscience, May 14, 2008, vol. 28, No. 20, pp. 5189-5194.
Keay et al., "The role of hCG in reproductive medicine," *BJOG.*, 111(11):1218-1228, Nov. 2004.
Kristiansen et al., "Introduction and Validation of DoloTest®: a new health-related quality of life tool used in pain patients," *Pain Pract.*, 10(5):396-403, Sep.-Oct. 2010.
Latremoliere and Woolf, "Central sensitization: a generator of pain hypersensitivity by central neural plasticity," *J Pain.*, 10(9):895-926, Sep. 2009.
Lei and Rao, "Neural actions of luteinizing hormone and human chorionic gonadotropin," *Semin Reprod Med.*, 19(1):103-109, 2001.
Lei et al., "Novel expression of human chorionic gonadotropm/luteinizing hormone receptor gene in brain." *Endocrinology.*, 132(5):2262-22770, May 1993.
Maletic and Raison, "Neurobiology of depression, fibromyalgia and neuropathic pain," *Front Biosci (Landmark Ed)*. 14:5291-5338, Jun. 2009.
Mayer et al., "The development and psychometric validation of the central sensitization inventory," *Pain Pract.*, 12(4):276-285, Epub Sep. 27, 2011.
Maymó et al., "Up-regulation of placental leptin by human chorionic gonadotropin," *Endocrinology*, 150(1):304-313, Epub Sep. 2008.
Meng et al., "Human chorionic gonadotropin induces neuronal differentiation of PC12 cells through activation of stably expressed Iutropin/choriogonadotropin receptor," *Endocrinology*, 148(12):5865-5873, print Dec. 2007, Epub Aug. 2007.
Narayan et al., "A biologically active single chain human chorionic gonadotropin analog with altered receptor binding properties," *Endocrinology* 141(1):67-71, Jan. 2000.
News Medical, "HCG hormone therapy may benefit patients with intractable pain," Mar. 25, 2011, Retrieved from the Internet: <URL: http://www.news-medical.net/news/20110325/HCG-hormone-therapy-may-benefit-patients-with-intractable-pain.aspx>, 1 page.
Nijs et al., "Treatment of central sensitization in patients with 'unexplained' chronic pain: what options do we have?" *Expert Opin Pharmacother.*, 12(7):1087-1098, Epub Jan. 2011.
Office Action in Australian Application No. 2016201537 dated Jan. 27, 2017, 5 pages.
Office Action in Japanese Application No. 2014-505405, dated Dec. 21, 2016, 3 pages with English translation.
Office Action in Mexican Application No. MX/a/2013/012078, summarization from foreign associate dated Mar. 13, 2017, 5 pages.
Patil and Nagaraj, "The effect of human chorionic gonadotropin (HCG) on functional recovery of spinal cord sectioned rats." *Acta Neurochir* (Wien)., 69(3-4):205-218, 1983.
Paulson and Gor, "Management of chronic pelvic pain," *Expert Rev. Obstet. Gynecol.*, 2(1): 37-50, Jan. 2007.
Peresada, "Predmenstrualny sindrom: novy vzglyad na rol magniya, Meditsinskie novosti," [Premenstrual syndrome: a new look at the role of magnesium] No. 9, pp. 35-38, 2003 Retrieved from the Internet: <URL: http://www.mednovosti.by/journal.aspx?Article=2426> [English machine translation], 9 pages.
Post, "Kindling and sensitization as models for affective episode recurrence, cyclicity, and tolerance phenomena," *Neurosci Biobehav Rev.*, 31(6):858-873, Epub Apr. 2007.
Puett et al., "Structure-function relationships of the luteinizing hormone receptor," *Ann N Y Acad Sci.*, 1061:41-54, Dec. 2005.
Rao and Lei, "The past, present and future of nongonadal LH/hCG actions in reproductive biology and medicine," *Mol Cell Endocrinol.*, 269(1-2):2-8, Epub Feb. 2007.
Recla et al., "New and emerging therapeutic agents for the treatment of fibromyalgia: an update," *J Pain Res.*, 3:89-103. Jul. 2010.
Remington, The Science and Practice of Pharmacy, 21st Edition, p. 2033, 2005.
Sher et al., "Decreased suicidal ideation in depressed patients with or without comorbid posttraumatic stress disorder treated with selective serotonin reuptake inhibitors: an open study," *Psychiatry Res.*, 196(2-3):261-266, Epub Mar. 6, 2012.

(56) References Cited

OTHER PUBLICATIONS

Simeons, *Pounds and Inches*, p. 24, retrieved front the Internet: URL:<http://www.hcgbodyshaper.com/simeon.pdf>, 1953.

Stella et al., *Prodrugs: Challenges and Rewards. Part 1*, p. 24, New York: Published by AAPS Press and Springer; 2007.

Stone et al., "In search of analgesia: emerging roles of GPCRs in pain," Oct. 2009 vol. 9, No. 5, pp. 234-251.

Tennant, "Hormone Therapies: Newest Advance in Pain Care", Practical Pain Management, May 2011, pp. 98-105.

Tennant, "Human Chorionic Gonadotropin in Pain Treatment," Practical Pain Management [online] Jun. 1, 2009. Retrieved from the Internet: <http://www.practicalpainmanagement.com/treatments/hormone-therapy/human-chorionic-gonadotropin-pain-treatment>, 5 pages.

Tennant, "Human Chorionic Gonadotropin in Pain Treatment," *Practical Pain Management.*, 9(5):44-46, Jun. 2009.

Tennant, "Human Chorionic Gonadotropin: Emerging Use in Pain Treatment," Prepared for Practical Pain Management, 10 pages [edited version published Jun. 1, 2009].

Tennant, "The use of hormones for chronic pain." *Journal of Prolotherapy,* 2(4):489-494, Nov. 2010.

Titelbaum, "End Fatigue: Update on using HCG to treat pain." Mar. 15, 2011, Retrieved from the Internet: <URL: http://www.jacobteitelbaum.com/health_articles_c_2/Cfs_fm-hcg-email-exchange-between-teitelbaum-and-tennant.html>, 3 pages.

Woolf, "Central sensitization: implications for the diagnosis and treatment of pain," *Pain,* 152(3 Suppl):S2-S15, Epub Oct. 2010.

Yang et al, "Pain Sensitization in Male Chronic Pelvic Pain Syndrome: Why are Symptoms so Difficult to Treat?," *J. Urol,* 170(3)823-827, Sep. 2003.

Yunis, "Fibromyalgia and overlapping disorders: the unifying concept of central setlsitivity syndromes," *Semin Arthritis Rheum.*, 36(6):339-356, Epub Mar. 2007.

Zreik et al., "Fertility drugs and the risk abreast cancer: a meta-analysis and review," *Breast Cancer Res Treat,* 124(1):13-26, print Nov. 2010, Epub Aug. 2010.

International Preliminary Report on Patentability in International Application No. PCT/US2015/060348, dated May 16, 2017, 7 pages.

* cited by examiner

TREATMENT OF DEPRESSION AND PTSD

CROSS-REFERENCE TO RELATED APPLICATIONS

This application is a continuation application of U.S. patent application Ser. No. 14/436,172, filed on Apr. 16, 2015, which is a National Stage application under 35 U.S.C. §371 of International Application No. PCT/US2013/065711, having an International Filing Date of Oct. 18, 2013, which claims the benefit of priority to U.S. Provisional Application No. 61/715,590, filed on Oct. 18, 2012. The disclosure of the prior application is considered part of (and is incorporated by reference in) the disclosure of this application.

BACKGROUND OF THE INVENTION

Field of the Invention

This invention relates to the treatment of depression and post traumatic stress disorder (PTSD).

Description of the Related Art

Chronic Pain, Central Sensitization, and Mood Disorders

An ongoing and pervasive problem in the medical community is treating patients with chronic pain syndromes. It is well recognized today that chronic pain is fundamentally different from acute pain, also referred to as nociceptive pain, that results from a mechanical, chemical, metabolic or inflammatory insult. Central sensitization is a newly recognized diagnostic entity that underlies a broad range of phenotypic syndromes, including various chronic pain and mood disorders. Central sensitization refers to an abnormal state of functioning of the neurons and circuitry of the central pain intensity, perception and modulation systems; due to synaptic, chemical, functional and/or structural changes, in which pain is no longer coupled, as acute nociceptive pain is, to particular peripheral stimuli. Instead, the central nervous system (CNS) initiates, maintains and contributes to the generation of pain hypersensitivity and perception even in the absence of a peripheral stimulus. See, for example, C J Woolf, "Central sensitization: Implications for the diagnosis and treatment of pain", *PAIN*, v. 152, pp. S2-S15 (2011).

Chronic pain and central sensitization represent an overlapping constellation of diagnostic conditions and syndromes. This may explain why there remains a critical lack of effective medical interventions to treat chronic pain disorders. Traditional pharmaceutical approaches generally deal with a single involved pathway, which tends to yield less than ideal results and is often associated with significant toxicity. For example, the treatment options most commonly investigated to date consist of centrally acting drugs. These include ketamine, dextromethorphan, gabapentin, pregabalin, duloxetine, milnacipran, lamotrigine; and not all of these have reached human trials at this time. Each has demonstrated a poor therapeutic index in trials.

It has been noted that major depressive disorder (MDD) and chronic pain syndrome often present as co-morbid conditions: 30-60% of cases in one report (M J Bair et al., "Association of depression and anxiety alone and in combination with chronic musculoskeletal pain in primary care patients", Psychosomatic Medicine, v. 70(8), pp. 890-897 (2008)). A recent review on this topic suggests that there may be a shared neurobiological basis of MDD, fibromyalgia, neuropathic pain, and other chronic pain syndromes (V Maletic et al., "Neurobiology of depression, fibromyalgia and neuropathic pain", Frontiers in Bioscience, v. 14, pp. 5291-5338 (2009). Robert Post first proposed that 'kindling' and sensitization may have similar neurobiological underpinnings, such as neuroplastic changes and alterations in gene expression (R M Post, "Kindling and sensitization as models for affective episode recurrence, cyclicity, and tolerance phenomenon", Neuroscience & Biobehavioral Reviews, v. 31(6), pp. 858-873 (2007)).

Depression and Post Traumatic Stress Disorder

Depression, as discussed here, represents two disorders: dysthymic disorder (DD), classified in the DSM-IV-TR (Diagnostic and Statistical Manual of Mental Disorders, Fourth Edition, Text Revision, American Psychiatric Association, Washington D.C., 2000) under code 300.4 (see DSM-IV-TR at pages 345-348 and 376-381), and major depressive disorder (MDD), classified in the DSM-IV-TR under code 296.3x (see DSM-IV-TR at pages 349-356 for a description of major depressive episode and pages 369-376 for MDD). Diagnostic criteria for DD are, in summary, (1) a depressed mood for most of the day for more days than not for at least 2 years; (2) the presence, while depressed, of symptoms such as sleep disturbances, fatigue, and feelings of hopelessness; (3) no continuous period of more than 2 months during the 2 years without the symptoms in (1) and (2); and no major depressive episode present in the first 2 years of the disturbance (i.e. so that the disorder is not better accounted for by MDD); diagnostic criteria for MDD are, in summary, the presence of at least one major depressive episode (the presence of 5 or more symptoms including at least one of depressed mood and loss of interest or pleasure present during the same 2-week period, representing a change from previous functioning; the symptoms causing clinically significant distress or impairment, and not due to the effects of a substance, medical condition, or bereavement) not better accounted for by other conditions and lack of manic, mixed, or hypomanic episodes. As the DSM-IV-TR notes (page 374), DD and MDD are differentiated based on severity, chronicity, and persistence, and "the differential diagnosis between them is made particularly difficult by the fact that the two disorders share similar symptoms . . . ". Depression is commonly pharmacologically treated with antidepressants (such as the selective serotonin reuptake inhibitors (SSRIs), serotonin/norepinephrine reuptake inhibitors (SNRIs), and norepinephrine/dopamine reuptake inhibitors (NDRIs)), and also with the atypical antidepressants, tricyclic antidepressants, or monoamine oxidase inhibitors (MAOIs), or other medications, generally if the SSRI/SNRI/NDRI antidepressants are unsuccessful.

Post traumatic stress disorder (PTSD) is an anxiety disorder characterized by the re-experiencing of an extremely traumatic event accompanied by symptoms of increased arousal and by the avoidance of stimuli associated with the trauma, classified in the DSM-IV-TR under code 309.81 (see DSM-IV-TR at pages 429 and 463-468). Diagnostic criteria for PTSD are, in summary, that (1) the person has been exposed to a traumatic event in which both the person experienced, witnessed, or was confronted with one or more events that involved actual or threatened death or serious injury or a threat to physical integrity and the person's response involved intense fear, helplessness, or horror; (2) the event is persistently re-experienced; (3) there is a persistent avoidance of stimuli associated with the trauma and numbing of general responsiveness (not present before the trauma); and (4) there are persistent symptoms of increased arousal (not present before the trauma) indicated by at least two of (i) difficulty falling or staying asleep, (ii) irritability or outbursts of anger, (iii) difficulty concentrating, (iv) hypervigilance, and (v) exaggerated startle response. PTSD is commonly pharmacologically treated with antidepressants (such as the SSRIs and SNRIs) and anxiolytics, sometimes acutely treated with antipsychotics, and insomnia and nightmares are sometimes treated with prazosin (an adrenergic α-blocker).

The usual pharmacological treatments for depression and PTSD are associated with a number of side effects, in particular the sexual side effects known with SSRIs and SNRIs, that may make them unattractive options for persons suffering from these disorders.

Pain Transmission and G-Protein Coupled Receptors

Pain transmission and modulation through the central nervous system network of neurons and support glial cells (microglia and astrocytes) is largely under the control of a large family of cellular receptors known as G-protein-coupled receptors (GPCRs). The function of these complex transmembrane receptors is to transduce extracellular stimuli into intracellular signaling including gene transcription. GPCRs modulate and/or mediate virtually all physiologic processes in eukaryotic organisms, including acute and chronic pain. An estimated 90% of all known GPCRs are expressed in the central nervous system. 80% of the currently proposed GPCR families have a known role in modulation of pain. Similarly, most of the identified genes associated with pain modulation are GPCR related genes (LS Stone et al., "In search of analgesia: Emerging role of GPCRs in pain", Molecular Interventions, v. 9(5), pp. 234-241 (2009)).

In the pharmaceutical development industry, the search for new analgesic and mood modulating targets has its foundation in establishing central nervous system receptor groups for which ligands can be identified, leading to the manufacture of pharmaceutical compounds to provide pain relief and mood improvement. Regarding analgesia, there are for example, several recognized GPCR sub-groups that have been established as templates for drug development. Opioid receptors, cannabinoid receptors, GABA receptors, and α2 adrenergic receptors are examples of such established receptors for analgesic drug development.

Human Chorionic Gonadotropin (hCG) and the LH/hCG Receptor

Human chorionic gonadotropin (hCG) is a is a hormone produced during pregnancy that is made by the developing placenta after conception, and later by the placental component syncytiotrophoblast. hCG shares a receptor with Luteinizing Hormone (LH), the LH/hCG receptor. This receptor is a GPCR. Both hormones are produced in the same cells in the pituitary gland. Both LH and hCG are produced continually throughout life in males and females.

hCG is now recognized to have pleiotropic actions throughout the body as evidenced by the documented presence of receptors for hCG in multiple cellular compartments including the central nervous system (CNS). See C V Rao, "An overview of the past, present, and future of non-gonadal LH/hCG actions in reproductive biology and medicine", Seminars in Reproductive Medicine, v. 19, pp. 7-17 (2001), and Z M Lei et al., "Neural actions of luteinizing hormone and human chorionic gonadotropin". Seminars in Reproductive Medicine, v. 19, pp. 103-109 (2001).

In the adult CNS, hCG receptors have been established to be present in the hippocampal formation, hypothalamus, cerebral cortex, brain stem, cerebellum, pituitary gland, neural retina, spinal cord and the ependymal region (Z M Lei et al., "Novel expression of human chorionic gonadotropin/luteinizing hormone receptor gene in brain", Endocrinology, v. 132, pp. 2262-2270 (1993). Both neurons and glial cells are shown to express receptors for hCG (Z M Lei et al., previously cited). It has been postulated that hCG may play an important signaling role in differentiation and development of tissue subsets from germ cell layering during the blastocyst stage (M J Gallego et al., "The Pregnancy Hormones HCG and Progesterone Induce Human Embryonic Stem Cell Proliferation and Differentiation into Neuroectodermal Rosettes", Stem Cell Research and Therapy, v. 1, p. 28 (2010)) to organ development during fetal life (M A Abdallah et al., "Human Fetal Non-Gonadal Tissues Contain HCG/LH Receptors", Journal of Clinical Endocrinology and Metabolism, v. 89, pp. 952-956 (2004)) and perhaps on some more subtle, yet clinically significant way, in adults. Recent evidence confirms the presence of hCG receptors in the adult CNS, and additional evidence supports hCG as a signaling hormone for tissue differentiation and growth. See C V Rao et al., "The past, present and future of non-gonadal LH/hCG actions in reproductive biology and medicine", Molecular and Cellular Endocrinology, v. 269(1-2), pp. 2-8 (2007).

As noted above, the luteinizing hormone/human chorionic gonadotropin (LH/hCG) receptor is a GPCR (LS Stone et al., previously cited). It has been specifically shown to complex with the Gαi/o group resulting in modulation of neurotransmission (L Hu et al., "Essential role of G protein-gated inwardly rectifying potassium channels in gonadotropin-induced regulation of GnRH neuronal firing and pulsatile neurosecretion", Journal of Biological Chemistry, v. 281(35), pp. 25231-25240 (2006)). Gαi/o proteins mediate the widespread inhibitory effects of many neurotransmitters and they mediate the effects of almost all analgesic GCPR agonists (L S Stone et al., previously cited). D. Puett et al., "Structure-Function Relationships of the Luteinizing Hormone Receptor", Annals of the New York Academy of Science, v. 1061, pp. 41-54 (2005), describe the LH/hCG receptor (which they refer to as the luteinizing hormone receptor) and studies on elucidating the mechanisms by which LH and hCG bind to it and activate it. They also describing transfected cells containing both wild-type and mutated LH/hCG receptors, and a single chain hCG-LH/hCG receptor complex containing a fusion protein of the two subunits of hCG linked to the LH/hCG receptor. X-L Meng et al., "Human Chorionic Gonadotropin Induces Neuronal Differentiation of PC12 Cells through Activation of Stably Expressed Lutropin/Choriogonadotropin Receptor", Endocrinology, v. 148(12), pp. 5865-5873 (2007), describe the transfection of the LH/hCG receptor into PC12 cells (a cell line extensively used for studying neuronal differentiation) that then stably express the receptor, and studies in those cells when treated with hCG or LH and optional inhibitors. Various techniques for evaluating the interaction between the LH and hCG ligands and the PC12 cells are described.

Pain Management with hCG

In a series of applications including U.S. Provisional Application No. 61/475,908, filed 15 Apr. 2011; U.S. application Ser. No. 13/211,101, filed 16 Aug. 2011; and U.S. application Ser. No. 13/311,250, "Methods for Chronic Pain Management and Treatment Using hCG", filed 5 Dec. 2011, there are described methods, etc. for the treatment of chronic pain or other central sensitization sequelae by the administration of hCG or its analogs or metabolites at doses equivalent to the subcutaneous administration of hCG at 50-200 IU/day, and 120-170 IU/day, preferably 140-160 IU/day.

The applications report that patients discontinued other analgesic agents and manifested a continued and improved analgesic response, confirming that another receptor group was indeed engaged to create the clinical response noted in that series. For example, the sedation, tolerance (requiring higher dosing for effect), constipation and addiction potential seen with chronic opiate administration was not seen in patients discontinuing opiate administration in favor of continued hCG administration, implying a different mechanism of action at a different analgesic receptor site for these patients.

The applications also suggest that hCG acts similarly on neural pathways involved in MDD that are subject to a very similar sensitization or 'kindling' phenomenon (implying that each episode of depression makes subsequent depressive episodes more likely and less dependent upon an external stimulus such as stress or sickness), where cellular structure and function are modulated and modified through many of the same CNS synaptic, cell signaling and transcriptional pathways, to effect depression.

The disclosures of the documents referred to in this application are incorporated into this application by reference.

SUMMARY OF THE INVENTION

In a first aspect, this invention is a method of treating at least one of depression and post traumatic stress disorder in a person suffering therefrom, comprising administering a compound that is hCG, or an hCG analog, or a prodrug or metabolite of hCG or an hCG analog, to the person, in an amount equivalent to a subcutaneous dose of 50-200 IU, preferably 120-170 IU, more preferably 140-160 IU, of hCG per day.

In other aspects, this invention thus includes:
(1) a method of treating at least one of depression and post traumatic stress disorder in a person suffering therefrom, comprising administering a composition containing a compound that is hCG, or an hCG analog, or a prodrug or metabolite of hCG or an hCG analog, to the person, in an amount equivalent to a subcutaneous dose of 50-200 IU, preferably 120-170 IU, more preferably 140-160 IU, of hCG per day;
(2) the use of a compound that is hCG, or an hCG analog, or a prodrug or metabolite of hCG or an hCG analog, in an amount equivalent to a subcutaneous dose of 50-200 IU, preferably 120-170 IU, more preferably 140-160 IU, of hCG per day, or a composition containing such compound, for the treatment of at least one of depression and post traumatic stress disorder;
(3) a kit containing a compound that is hCG, or an hCG analog, or a prodrug or metabolite of hCG or an hCG analog, or a composition containing such compound, with instructions to administer the compound or composition in an amount equivalent to a subcutaneous dose of 50-200 IU, preferably 120-170 IU, more preferably 140-160 IU, of hCG per day; and
(4) a method of prescribing or supplying to a person suffering from a condition that is at least one of depression and post traumatic stress disorder a treatment for that condition that comprises administering a composition containing a compound that is hCG, or an hCG analog, or a prodrug or metabolite of hCG or an hCG analog, to the person, in an amount equivalent to a subcutaneous dose of 50-200 IU, preferably 120-170 IU, more preferably 140-160 IU, of hCG per day.

In other aspects this invention also includes:
(5) treating at least one of depression and post traumatic stress disorder in a person suffering therefrom by activating the central nervous system LH/hCG receptor; and
(6) treating at least one of depression and post traumatic stress disorder in a person suffering therefrom by modulating the central sensitization pathway.

Preferred embodiments of this invention are characterized by the specification and by the features of claims 2 to 18 of this application as filed. In particular, for each of the other aspects, the preferences are to be taken as the same as those expressed in the specification and claims for the first aspect of the invention.

DETAILED DESCRIPTION OF THE INVENTION

Definitions

"Human chorionic gonadotropin" or "hCG" includes both hCG obtained from the urine of pregnant women (uHCG) and hCG prepared in bacterial, yeast, plant, or mammalian cell cultures utilizing recombinant DNA hybridization techniques (rHCG).

An "hCG analog" is a compound having the biological activity of hCG in the treatment of depression and/or post traumatic stress disorder and that is either: (i) a modified hCG (such as a truncated, elaborated, or chemically modified—as by amino acid substitution—hCG), or (ii) a compound that can bind to the LH/hCG receptor to produce the same effect as hCG.

A "prodrug" of hCG is hCG modified such that the modified hCG is converted within a target cell or target organ/anatomic structure into hCG so as to achieve the effect of hCG administration; a prodrug of an hCG analog is similarly defined. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the invention can be modified in numerous manners, and especially preferred modifications include those that improve one or more pharmacokinetic and/or pharmacodynamic parameters. For example, one or more substituents may be added or replaced to achieve a higher bioavailability.

A "metabolite" of hCG is a compound resulting from in vivo metabolism of hCG (for example, via proteolytic digest, glycosylation, hydroxylation, phosphorylation, sulfuration, etc), where the metabolite produces the effect of hCG administration; a metabolite of an hCG analog is similarly defined.

"Comprising" or "containing" and their grammatical variants are words of inclusion and not of limitation and mean to specify the presence of stated components, groups, steps, and the like but not to exclude the presence or addition of other components, groups, steps, and the like. Thus "comprising" does not mean "consisting of", "consisting substantially of", or "consisting only of"; and, for example, a formulation "comprising" a compound must contain that compound but also may contain other active ingredients and/or excipients.

"Treating" or "treatment" of a condition includes one or more of:
(1) inhibiting development of the condition, e.g., arresting its development,
(2) relieving the condition, e.g., causing regression of or curing the condition,
(3) preventing recurrence of the condition, and
(4) palliating symptoms of the condition.

Salts

Salts (for example, pharmaceutically acceptable salts) of the compounds of this invention (i.e. hCG, or an hCG analog, or a prodrug or metabolite of hCG or an hCG analog) are included within the compounds of this invention and are useful in the compositions, methods, and uses described in this application. Such salts are preferably formed with pharmaceutically acceptable acids. See, for example, Stahl and Wermuth, eds., "Handbook of Pharmaceutically Acceptable Salts", (2002), Verlag Helvetica Chimica Acta, Zürich, Switzerland, for an extensive discussion of pharmaceutical salts, their selection, preparation, and use. Unless the context requires otherwise, reference to any compound of this invention is a reference both to the compound and to its salts.

These salts include salts that may be formed when acidic protons present are capable of reacting with inorganic or organic bases. Typically the parent compound is treated with an excess of an alkaline reagent, such as hydroxide, carbonate or alkoxide, containing an appropriate cation. Cations such as Na+, K+, Ca2+, Mg2+ and NH4+ are examples of cations present in pharmaceutically acceptable salts. Suitable inorganic bases, therefore, include calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

If a compound contains a basic group, such as an amino group, it may be prepared as an acid addition salt. Acid addition salts of the compounds are prepared in a standard manner in a suitable solvent from the parent compound and an excess of an acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, 4-toluenesulfonic acid, hexanoic acid, heptanoic acid, cyclopentanepropionic acid, lactic acid, 2-(4-hydroxybenzoyl)benzoic acid, 1,2-ethanedisulfonic acid, 2-hydroxyethanesulfonic acid, benzenesulfonic acid, 4-chlorobenzenesulfonic acid, 2-naphthalenesulfonic acid, camphorsulfonic acid, 4-methylbicyclo[2.2.2]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, tert-butylacetic acid, laurylsulfuric acid, glucuronic acid, glutamic acid, 3-hydroxy-2-naphthoic acid, stearic acid, muconic acid and the like.

Compositions and Dosing

Pharmaceutical compositions comprising the compounds of this invention include a compound that is hCG, or an hCG analog, or a prodrug or metabolite of hCG or an hCG analog, and optionally a pharmaceutically acceptable excipient.

The compounds may be administered by any route suitable to the person being treated and the nature of the person's condition. Routes of administration include administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in Remington: The Science and Practice of Pharmacy, 20th ed., A. Gennaro, ed., Lippincott Williams & Wilkins, Philadelphia, Pa., U.S.A. Typical formulations will be either oral or solutions for injection, especially subcutaneous injection. Typical dosage forms will be tablets or capsules for oral administration, solutions for injection, and lyophilized powders for reconstitution as solutions for injection.

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active compound(s) and which is not toxic or otherwise undesirable to the subject to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet (including an orally-disintegrating tablet) or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. Orally-disintegrating tablets will generally include excipients such as mannitol or another sugar as the primary diluent, a disintegrating agent such as crospovidone or gelatin, and microcrystalline cellulose. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The pharmaceutical compositions of this invention may also be formulated in lyophilized form for parenteral administration. Lyophilized formulations may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition. Typically, a pharmaceutical composition of the present invention is packaged in a container with a label, or instructions, or both, indicating use of the pharmaceutical composition for the treatment of depression and/or post traumatic stress disorder and indicating dosing in an amount equivalent to a subcutaneous dose of 50-200 IU, preferably 120-170 IU, more preferably 140-160 IU, of hCG per day. The dosing may be determined based on once/day dosing of the compound or more frequent dosing, but will preferably be based on once/day or at least not more than twice/day dosing, as a matter of patient convenience.

A person of ordinary skill in the art will have no difficulty, considering that skill and this disclosure, in determining appropriate dosing for a compound that is hCG, an hCG analog, or a prodrug or metabolite of hCG or an hCG analog, by administering such a compound to a person suffering from depression or post traumatic stress disorder; and will also have no difficulty, considering that skill and this disclosure, in formulating compositions of the compounds for such use.

hCG itself is available, by prescription in the United States, in lyophilized powdered form in 5,000 IU or 10,000 IU vials for reconstitution from various sources under brand names such as NOVAREL® (Ferring Pharmaceuticals), PREGNYL® (Organon), and others.

Treatment of Depression and Post Traumatic Stress Disorder

In the first aspect, this invention is a method of treating at least one of depression and post traumatic stress disorder in a person suffering therefrom, comprising administering a compound that is hCG, or an hCG analog, or a prodrug or metabolite of hCG or an hCG analog, to the person, in an amount equivalent to a subcutaneous dose of 50-200 IU, preferably 120-170 IU, more preferably 140-160 IU, of hCG per day.

The treatment preferably comprises once/day administration of the compound, such as by a once/day subcutaneous injection of hCG at a dose of 50-200 IU, preferably 120-170 IU, more preferably 140-160 IU; but may comprise administration more frequently of divided doses of the compound in an amount equivalent to a subcutaneous dose of 50-200 IU, preferably 120-170 IU, more preferably 140-160 IU, of hCG per day.

In a study of 24 persons treated with 150 IU/day of hCG subcutaneously for 6 weeks for weight loss (14 persons) or pain control (10 persons) reported in application Ser. No. 13/311,250 referred to previously, patients were assessed with the DoloTest™, a test instrument used to assess pain and health-related quality of life issues. See K Kristiansen et al., "Introduction and Validation of DoloTest: A Health Related Quality of Life Tool Used in Pain Patients", Pain Practice, v. 10(5), pp. 396-403 (2010); and see also www-.dolotest.dk. There were statistically significant improvements in scores relating to depressive symptoms (reduced energy and strength, low spirit, reduced social life, and problems sleeping) over the group, indicating the usefulness of hCG, and expected use of its analogs and prodrugs and metabolites, for the treatment of depression. In addition, a small number of persons suffering from PTSD treated by the inventors with hCG in the same manner displayed an improvement in their PTSD symptoms.

No hCG gonadal treatment-associated side effects were observed; and no hCG-related effects are expected at this low dose. Notably, in the above series patients who had been placed on antidepressant medications for mood disorders and/or chronic pain syndromes at the time of initiating hCG treatment, no longer required these medications after initiating hCG treatment, and were free of untoward side effects associated with these medications. For example, one patient had previously been placed on LEXAPRO® (escitalopram oxalate, an SSRI) for depression and struggled with anorgasmia associated with taking this medication. On hCG treatment and no longer needing to take LEXAPRO®, this patient reported clear improvement in mood and a return to orgasmic function, which has been of significant value to him. These responses imply the activation of an alternate receptor group in the action of hCG in treating depression and PTSD.

Although improvement in symptoms may be seen rapidly, and though some persons treated for pain control did not require continuing treatment beyond their initial 6 week course of treatment, most did; and the inventors expect that treatment for depression and/or PTSD will typically last at least 1 week, preferably at least 3 weeks, more preferably at least 6 weeks, and will generally be continuing/chronic, with administration of the compound daily. As with other antidepressant treatments, it is possible that patients treated chronically for a long time (for example, months or more) may be able to terminate hCG treatment without a recurrence of their symptoms, and this may be tested on a case-by-case basis in a manner consistent with normal medical practice: if there is a relapse on cessation of treatment, the treatment may be resumed and will be effective again.

Although age, gender and weight of recipients of hCG treatment for chronic pain and weight loss does not appear with current studies to affect the preferred therapeutic ranges, it is contemplated that the amount of compound that is administered and the dosage regimen for treating a disease condition with the compounds and/or compositions of this invention for treating at least one of depression and post traumatic stress disorder may depend on one of more of a variety of factors, including the age, weight, sex and medical condition of the subject, the severity of the disease, the route and frequency of administration, and the particular compound employed, and thus may vary.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:

1. A method of treating depression or post traumatic stress disorder in a subject suffering therefrom, comprising subcutaneously administering to the subject hCG in an amount of 50 IU per day to 200 IU per day, wherein the method of treating includes treating at least one symptom of the depression or post traumatic stress disorder.

2. The method of claim 1, wherein the method comprises treating depression.

3. The method of claim 1, wherein the method comprises treating post traumatic stress disorder.

4. The method of claim 1 wherein the amount of hCG that is administered is a subcutaneous dose of between 120 IU per day and 170 IU per day of hCG.

5. The method of claim 4 wherein the amount of hCG that is administered is a subcutaneous dose of between 140 IU per day and 160 IU per day of hCG.

6. The method of claim 1 where the compound is administered once per day.

7. The method of claim 1 where the compound is administered once daily for at least 1 week.

8. The method of claim 7 where the compound is administered once daily for at least 3 weeks.

9. The method of claim 8 where the compound is administered once daily for at least 6 weeks.

10. The method of claim 9 where the compound is administered chronically.

11. The method of claim 1, wherein the subcutaneous dose consists essentially of hCG.

12. The method of claim 1, wherein the method comprises treating dysthymic disorder.

13. The method of claim 1, wherein the method comprises treating major depressive disorder.

* * * * *